US008852643B2

(12) United States Patent
Gonzales et al.

(10) Patent No.: US 8,852,643 B2
(45) Date of Patent: *Oct. 7, 2014

(54) LIQUID CLEANING AND/OR CLEANSING COMPOSITION

(75) Inventors: Denis Alfred Gonzales, Brussels (BE); Aicha Dkidak, Brussels (BE); Martin Ian James, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 96 days.

This patent is subject to a terminal disclaimer.

(21) Appl. No.: 13/526,605

(22) Filed: Jun. 19, 2012

(65) Prior Publication Data

US 2012/0321681 A1    Dec. 20, 2012

Related U.S. Application Data

(60) Provisional application No. 61/498,741, filed on Jun. 20, 2011.

(51) Int. Cl.
| | | |
|---|---|---|
| A61K 9/14 | (2006.01) | |
| A61K 9/50 | (2006.01) | |
| A61K 8/02 | (2006.01) | |
| C11D 17/00 | (2006.01) | |
| A61K 8/85 | (2006.01) | |
| A61Q 11/00 | (2006.01) | |
| C11D 3/14 | (2006.01) | |
| C11D 3/37 | (2006.01) | |
| A61Q 5/02 | (2006.01) | |
| A61K 8/04 | (2006.01) | |

(52) U.S. Cl.
CPC .............. *C11D 3/3715* (2013.01); *C11D 17/00* (2013.01); *A61K 8/85* (2013.01); *A61K 2800/654* (2013.01); *A61Q 11/00* (2013.01); *C11D 3/14* (2013.01); *A61K 8/0245* (2013.01); *A61K 2800/412* (2013.01); *C11D 17/0013* (2013.01); *A61Q 5/02* (2013.01); *A61K 8/04* (2013.01); *A61K 2800/28* (2013.01)
USPC ........................... 424/489; 424/401; 424/501

(58) Field of Classification Search
None
See application file for complete search history.

(56) References Cited

U.S. PATENT DOCUMENTS

| | | | |
|---|---|---|---|
| 1,621,906 A | 3/1927 | Schless | |
| 2,082,275 A | 6/1937 | Daimler et al. | |
| 2,084,632 A | 6/1937 | Ellis | |
| 2,255,082 A | 9/1941 | Orthner et al. | |
| 2,438,091 A | 3/1948 | Lynch | |
| 2,528,378 A | 10/1950 | Mannheimer | |
| 2,658,072 A | 11/1953 | Kosmin | |
| 2,702,279 A | 2/1955 | Funderburk et al. | |
| 3,070,510 A | 12/1962 | Cooley et al. | |
| 3,586,715 A | 6/1971 | Smeets | |
| 3,812,044 A | 5/1974 | Connor et al. | |
| 3,915,903 A | 10/1975 | Wise | |
| 3,929,678 A | 12/1975 | Laughlin et al. | |
| 3,985,668 A | 10/1976 | Hartman | |
| 4,025,444 A | 5/1977 | Murphy et al. | |
| 4,051,056 A | 9/1977 | Hartman | |
| 4,088,620 A | 5/1978 | Nihongi et al. | |
| 4,102,992 A | 7/1978 | Davis | |
| 4,240,919 A | 12/1980 | Chapman | |
| 4,298,490 A | 11/1981 | Lange et al. | |
| 4,309,316 A | 1/1982 | Lange et al. | |
| 4,473,611 A | 9/1984 | Haq | |
| 4,481,126 A | 11/1984 | Trinh et al. | |
| 4,537,604 A | 8/1985 | Dawson | |
| 4,565,644 A | 1/1986 | Smith et al. | |
| 4,565,647 A | 1/1986 | Llenado | |
| 4,581,385 A | 4/1986 | Smith et al. | |
| 4,657,692 A | 4/1987 | Choy et al. | |
| 4,663,069 A | 5/1987 | Llenado | |
| 4,676,920 A | 6/1987 | Culshaw | |
| 4,704,233 A | 11/1987 | Hartman et al. | |
| 4,767,563 A | 8/1988 | De Buzzaccarini | |
| 4,772,425 A | 9/1988 | Chirash et al. | |
| 4,842,763 A | 6/1989 | Troger et al. | |
| 4,906,396 A | 3/1990 | Falholt et al. | |
| 4,988,369 A * | 1/1991 | Akay | 51/293 |
| 5,287,207 A | 2/1994 | Mulkens et al. | |
| 5,500,451 A | 3/1996 | Goldman et al. | |
| 5,776,872 A | 7/1998 | Giret et al. | |
| 5,776,878 A | 7/1998 | Thoen | |
| 5,798,505 A | 8/1998 | Lee | |
| 5,821,214 A | 10/1998 | Weibel | |
| 5,830,445 A | 11/1998 | Bouillon et al. | |
| 5,883,062 A | 3/1999 | Addison et al. | |
| 5,898,026 A | 4/1999 | Yianakopoulos et al. | |
| 5,906,973 A | 5/1999 | Ouzounis et al. | |
| 6,008,181 A | 12/1999 | Cripe et al. | |

(Continued)

FOREIGN PATENT DOCUMENTS

| | | |
|---|---|---|
| DE | 24 10 425 A1 | 10/1974 |
| DE | 10 2004 038771 A1 | 8/2005 |

(Continued)

OTHER PUBLICATIONS

U.S. Appl. No. 13/517,837, filed Jun. 14, 2012, Gonzales et al.
U.S. Appl. No. 13/517,728, filed Jun. 14, 2012, Gonzales et al.
U.S. Appl. No. 13/526,592, filed Jun. 19, 2012, Gonzales et al.
U.S. Appl. No. 13/526,596, filed Jun. 19, 2012, Gonzales et al.
U.S. Appl. No. 13/517,746, filed Jun. 14, 2012, Gonzales et al.
U.S. Appl. No. 13/526,613, filed Jun. 19, 2012, Gonzales et al.
U.S. Appl. No. 13/517,762, filed Jun. 14, 2012, Perez-Prat Vinuesa et al.
U.S. Appl. No. 13/621,858, filed Sep. 18, 2012, Gonzales et al.
U.S. Appl. No. 13/621,860, filed Sep. 18, 2012, Perez-Prat Vinuesa et al.

(Continued)

*Primary Examiner* — Susan Tran
(74) *Attorney, Agent, or Firm* — John T. Dipre; Steven W. Miller

(57) ABSTRACT

The present invention relates to a liquid, cleaning and/or cleansing composition comprising biodegradable abrasive cleaning particles.

19 Claims, 1 Drawing Sheet

(56) References Cited

U.S. PATENT DOCUMENTS

| | | |
|---|---|---|
| 6,020,303 A | 2/2000 | Cripe et al. |
| 6,060,443 A | 5/2000 | Cripe et al. |
| 6,080,707 A | 6/2000 | Glenn et al. |
| 6,132,212 A | 10/2000 | Horiguchi et al. |
| 6,221,829 B1 | 4/2001 | Symes et al. |
| 6,242,405 B1 | 6/2001 | Lykke et al. |
| 6,265,363 B1 | 7/2001 | Viscovitz |
| 6,268,325 B1 | 7/2001 | Luciani et al. |
| 6,274,540 B1 | 8/2001 | Scheibel et al. |
| 6,299,746 B1 | 10/2001 | Conte et al. |
| 6,306,817 B1 | 10/2001 | Kott et al. |
| 6,359,031 B1 | 3/2002 | Lykke et al. |
| 6,369,121 B1 | 4/2002 | Catalfamo et al. |
| 6,444,716 B1 | 9/2002 | Hird et al. |
| 6,514,926 B1 | 2/2003 | Kott et al. |
| 6,525,233 B1 | 2/2003 | Connor et al. |
| 6,537,957 B1 | 3/2003 | Cardola et al. |
| 6,566,319 B1 | 5/2003 | Scheibel et al. |
| 6,583,096 B1 | 6/2003 | Kott et al. |
| 6,593,285 B1 | 7/2003 | Scheibel et al. |
| 6,602,840 B1 | 8/2003 | Scheibel et al. |
| 6,699,963 B2 | 3/2004 | Noda et al. |
| 6,749,066 B2 | 6/2004 | Bergman |
| 6,759,377 B2 | 7/2004 | Hackenthal et al. |
| 6,767,878 B1 | 7/2004 | Paye et al. |
| 6,808,759 B1 | 10/2004 | Okumura et al. |
| 6,858,216 B2 | 2/2005 | Schulze zur Wiesche et al. |
| 7,307,055 B2 | 12/2007 | Cook et al. |
| 7,393,820 B2 | 7/2008 | Soldanski et al. |
| 7,713,921 B2 | 5/2010 | Boutique et al. |
| 7,994,111 B2 | 8/2011 | Caggioni et al. |
| 2002/0137647 A1 | 9/2002 | Hackenthal et al. |
| 2002/0166832 A1 | 11/2002 | Silud et al. |
| 2002/0173243 A1 | 11/2002 | Costas et al. |
| 2003/0176633 A1 | 9/2003 | Noda et al. |
| 2003/0215417 A1 | 11/2003 | Uchiyama et al. |
| 2004/0216388 A1 | 11/2004 | Mathur et al. |
| 2004/0266645 A1 | 12/2004 | Albrecht et al. |
| 2005/0065056 A1 | 3/2005 | Cook et al. |
| 2005/0130873 A1 | 6/2005 | Cheung et al. |
| 2005/0170979 A1 | 8/2005 | Massaro et al. |
| 2005/0201965 A1 | 9/2005 | Kuhlman et al. |
| 2006/0011885 A1 | 1/2006 | Christmas et al. |
| 2006/0094635 A1 | 5/2006 | Pereira |
| 2006/0177488 A1 | 8/2006 | Caruso et al. |
| 2007/0006391 A1 | 1/2007 | Ghosh et al. |
| 2007/0010415 A1 | 1/2007 | Kinscherf et al. |
| 2007/0041927 A1 | 2/2007 | Blaeser et al. |
| 2007/0043147 A1 | 2/2007 | Higgins et al. |
| 2007/0135645 A1 | 6/2007 | Ignatyev et al. |
| 2007/0138671 A1 | 6/2007 | Anastasiou et al. |
| 2007/0167345 A1 | 7/2007 | Soldanski et al. |
| 2007/0191256 A1 | 8/2007 | Fossum et al. |
| 2007/0270730 A1 | 11/2007 | Rische et al. |
| 2008/0108714 A1 | 5/2008 | Swazey et al. |
| 2008/0139702 A1 | 6/2008 | De Almeida et al. |
| 2008/0149137 A1 | 6/2008 | Steinbrenner et al. |
| 2008/0248144 A1 | 10/2008 | Guenter et al. |
| 2009/0176935 A1 | 7/2009 | Boeckh et al. |
| 2009/0253816 A1 | 10/2009 | Nascimento et al. |
| 2009/0291306 A1 | 11/2009 | Quadbeck-Seeger |
| 2009/0325837 A1 | 12/2009 | Mundschau et al. |
| 2010/0081604 A1 | 4/2010 | Barger et al. |
| 2010/0081605 A1 | 4/2010 | Barger et al. |
| 2010/0081606 A1 | 4/2010 | Barger et al. |
| 2010/0197553 A1 | 8/2010 | Barnabas et al. |
| 2011/0021398 A1 | 1/2011 | Allef et al. |
| 2011/0039744 A1 | 2/2011 | Heath et al. |
| 2011/0150787 A1* | 6/2011 | Gonzales et al. ............... 424/49 |
| 2011/0150788 A1 | 6/2011 | Gonzales et al. |
| 2011/0150949 A1 | 6/2011 | Gonzales et al. |
| 2011/0150950 A1 | 6/2011 | Gonzales et al. |
| 2011/0150951 A1 | 6/2011 | Gonzales et al. |
| 2011/0178196 A1 | 7/2011 | Steinke et al. |
| 2011/0189414 A1 | 8/2011 | Whitehouse |
| 2011/0262371 A1 | 10/2011 | Deleersnyder et al. |
| 2011/0262504 A1 | 10/2011 | Deleersnyder et al. |
| 2011/0287105 A1 | 11/2011 | Gittleman |
| 2012/0029519 A1 | 2/2012 | Sengun et al. |
| 2012/0066851 A1 | 3/2012 | Gonzales et al. |
| 2012/0071378 A1 | 3/2012 | Gonzales et al. |
| 2012/0071379 A1 | 3/2012 | Gonzales et al. |
| 2012/0071380 A1 | 3/2012 | Gonzales et al. |
| 2012/0071383 A1 | 3/2012 | Perez-Prat Vinuesa et al. |
| 2012/0202730 A1 | 8/2012 | Allef et al. |
| 2012/0322713 A1* | 12/2012 | Perez-Prat Vinuesa et al. ............... 510/236 |

FOREIGN PATENT DOCUMENTS

| | | |
|---|---|---|
| DE | 10 2005 023801 A1 | 11/2006 |
| EP | 1 136 063 A2 | 9/2001 |
| EP | 1 460 125 A1 | 9/2004 |
| GB | 2 001 099 A | 1/1979 |
| GB | 2 126 999 A | 4/1984 |
| GB | 2 145 729 A | 4/1985 |
| JP | 59192526 A | 10/1984 |
| JP | 10025239 A | 1/1998 |
| JP | 2005 296822 A | 10/2005 |
| JP | 2007 077311 A | 3/2007 |
| JP | 2009 160717 A | 7/2009 |
| WO | WO 91/14420 A1 | 10/1991 |
| WO | WO 99/05084 A1 | 2/1999 |
| WO | WO 99/52500 A1 | 10/1999 |
| WO | WO 01/31110 A1 | 5/2001 |
| WO | WO 02/38720 A1 | 5/2002 |
| WO | WO 2004/071483 A1 | 8/2004 |
| WO | WO 2008/109270 A1 | 9/2008 |

OTHER PUBLICATIONS

ASTM Designation: F1877-05 Jun. 10, 2009; Standard Practice for Characterization of Particles; 14 pages; chapter 11.3.6; Section 11.3. 2.

International Standard; ISO 9276-6:2008(E) section 8.2; section 7; Representation of results of particle size analysis—Part 6: Descriptive and quantitative representation of particle shape and morphology.

"Vegetable Ivory", W.P. Armstrong, (http://waynesword.palomar.edu/pljan99.htm), 2012.

"Phytelephas", Wikipedia.org (http://en.wikipedia.org/wiki/Phytelephas), 2012.

* cited by examiner

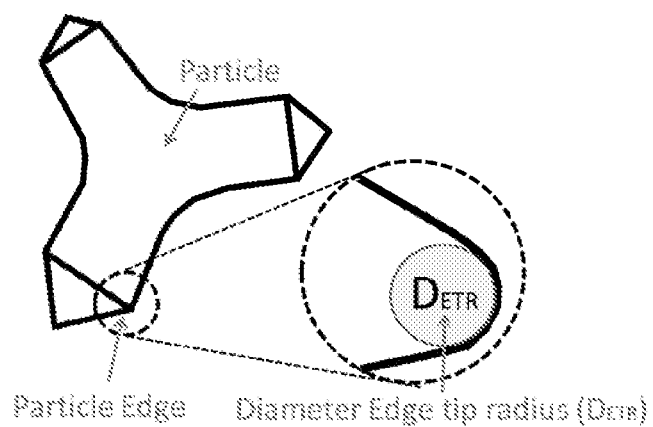

LIQUID CLEANING AND/OR CLEANSING COMPOSITION

CROSS REFERENCE TO RELATED APPLICATION

This application claims the benefit of U.S. Provisional Application No. 61/498,741, filed Jun. 20, 2011.

TECHNICAL FIELD

The present invention relates to liquid compositions for cleaning and/or cleansing a variety of inanimate and animate surfaces, including hard surfaces in and around the house, dish surfaces, car and vehicles surfaces, surfaces in the oral cavity such as teeth etc. More specifically, the present invention relates to liquid scouring compositions comprising suitable particles for cleaning and/or cleansing.

BACKGROUND OF THE INVENTION

Scouring compositions such as particulate compositions or liquid (incl. gel, paste-type) compositions containing abrasive components are well known in the art. Such compositions are used for cleaning and/or cleansing a variety of surfaces; especially those surfaces that tend to become soiled with difficult to remove stains and soils.

Amongst the currently known scouring compositions, the most popular ones are based on abrasive particles with shapes varying from spherical to irregular. The most common abrasive particles are either inorganic like carbonate salt, clay, silica, silicate, shale ash, perlite and quartz sand or organic polymeric beads like polypropylene, PVC, melamine, urea, polyacrylate and derivatives, and come in the form of liquid composition having a creamy consistency with the abrasive particles suspended therein.

The surface safety profile of such currently known scouring compositions is inadequate alternatively, poor cleaning performances is shown for compositions with an adequate surface safety profile. Indeed, due to the presence of very hard abrasive particles, these compositions can damage, i.e., scratch, the surfaces onto which they have been applied while with less hard material the level of cleaning performance is insufficient. Indeed, the formulator needs to choose between good cleaning/cleansing performance but featuring strong surface damage or compromising on the cleaning/cleansing performance while featuring an acceptable surface safety profile. In addition, such currently known scouring compositions at least in certain fields of application (e.g., hard surface cleaning) are perceived by consumers as outdated.

Furthermore, at least some of the above mentioned abrasives particles are not water soluble and remain in particulate form within tap water after use. Indeed, abrasive particles can flow into waste water pipes, wherein the abrasive particles will cluster and may cause blockages, and/or the abrasive particles may cause problems in waste water treatment and eventually may be deposited in soil or landfills. Thus, it has been determined that there is a need to further improve currently known scouring compositions with regard to the degradation properties of the abrasive material therein. Namely, by substituting the currently known abrasive material with material providing improved degradation process. Indeed, the use of abrasive material that undergoes rapid degradation even in mild biomedia, e.g.: like "readily biodegradable" material is highly desirable. Such readily biodegradable material is usually meeting biodegradation test and success criteria as described in ASTM6400 test method or ISO 148551 test method.

It is thus an objective of the present invention to provide a liquid cleaning and/or cleansing composition suitable to clean/cleanse a variety of surfaces, including inanimate surfaces, such hard surfaces in and around the house, dish surfaces, etc., wherein the abrasive particles are fully or partially biodegradable according to ASTM6400 test method or ISO 148551 test method, preferably according to ASTM6400 test method.

It has been found that the above objective can be met by the composition according to the present invention.

It is an advantage of the compositions according to the present invention that they may be used to clean/cleanse inanimate surfaces made of a variety of materials like glazed and non-glazed ceramic tiles, enamel, stainless steel, Inox®, Formica®, vinyl, no-wax vinyl, linoleum, melamine, glass, plastics, painted surfaces and the like, and animate surfaces like human and animal hair, hard and soft tissue surface of the oral cavity, such as teeth, gums, tongue and buccal surfaces, and the like.

Another advantage of the present invention is that the composition provides good cleaning/cleansing performance, whilst providing a good surface safety profile.

A further advantage of the present invention is that in the compositions herein, the particles can be formulated at very low levels, whilst still providing the above benefits. Indeed, in general for other technologies, high levels of abrasive particles are needed to reach good cleaning/cleansing performance, thus leading to high formulation and process cost, incompatibility with many package e.g.: squeeze or spray bottle, low incident usage ergonomy, difficult rinse and end cleaning profiles, as well as limitation for aesthetics and a pleasant hand feel of the cleaning/cleansing composition.

SUMMARY OF THE INVENTION

The present invention relates to a liquid cleaning and/or cleansing composition comprising biodegradable abrasive cleaning particles comprising a biodegradable aliphatic polyester comprising aliphatic dicarboxylic acid monomer or mixtures thereof and alkanediol monomer or mixtures thereof, wherein said biodegradable abrasive cleaning particles have a mean circularity from 0.1 to 0.6, wherein the circularity is measured according to ISO 9276—and mean solidity from 0.4 to 0.9, wherein mean solidity is measured according to ISO 9276-6, and wherein said biodegradable abrasive cleaning particles have a biodegradable rate above 50% according to ASTM6400 test method.

The present invention further encompasses a process of cleaning and/or cleansing a surface with a liquid, cleaning and/or cleansing composition comprising abrasive cleaning particles, wherein said surface is contacted with said composition, preferably wherein said composition is applied onto said surface.

BRIEF DESCRIPTION OF THE FIGURES

FIG. 1 is an illustration of tip radius.

DETAILED DESCRIPTION OF THE INVENTION

The Liquid Cleaning/Cleansing Composition

The compositions according to the present invention are designed as cleaners/cleansers for a variety of inanimate and animate surfaces. Preferably, the compositions herein are suitable for cleaning/cleansing inanimate surfaces.

In a preferred embodiment, the compositions herein are suitable for cleaning/cleansing inanimate surfaces selected from the group consisting of household hard surfaces; dish surfaces; surfaces like leather or synthetic leather; and automotive vehicles surfaces.

In another preferred embodiment, the compositions herein are suitable for cleaning/cleansing animate surfaces, preferably selected from the group consisting of human and animal hair, hard and soft tissue surface of the oral cavity, such as teeth, gums, tongue and buccal surfaces.

In a highly preferred embodiment, the compositions herein are suitable to clean household hard surfaces.

By "household hard surface", it is meant herein any kind of surface typically found in and around houses like kitchens, bathrooms, e.g., floors, walls, tiles, windows, cupboards, sinks, showers, shower plastified curtains, wash basins, WCs, fixtures and fittings and the like made of different materials like ceramic, vinyl, no-wax vinyl, linoleum, melamine, glass, Inox®, Formica®, any plastics, plastified wood, metal or any painted or varnished or sealed surface and the like. Household hard surfaces also include household appliances including, but not limited to refrigerators, freezers, washing machines, automatic dryers, ovens, microwave ovens, dishwashers and so on. Such hard surfaces may be found both in private households as well as in commercial, institutional and industrial environments.

By "dish surfaces" it is meant herein any kind of surfaces found in dish cleaning, such as dishes, cutlery, cutting boards, pans, and the like. Such dish surfaces may be found both in private households as well as in commercial, institutional and industrial environments.

The compositions according to the present invention are liquid compositions as opposed to a solid or a gas. Liquid compositions include compositions having a water-like viscosity as well as thickened compositions, such as gels and pastes.

In a preferred embodiment herein, the liquid compositions herein are aqueous compositions. Therefore, they may comprise from 65% to 99.5% by weight of the total composition of water, preferably from 75% to 98% and more preferably from 80% to 95%.

In an another preferred embodiment herein, the liquid compositions herein are mostly non-aqueous compositions although they may comprise from 0% to 10% by weight of the total composition of water, preferably from 0% to 5%, more preferably from 0% to 1% and most preferably 0% by weight of the total composition of water.

In a preferred embodiment herein, the compositions herein are neutral compositions, and thus have a pH, as is measured at 25° C., of 6-8, more preferably 6.5-7.5, even more preferably 7.

In other preferred embodiment compositions have pH preferably above pH 4 and alternatively have pH preferably below pH 9.

Accordingly, the compositions herein may comprise suitable bases and acids to adjust the pH.

A suitable base to be used herein is an organic and/or inorganic base. Suitable bases for use herein are the caustic alkalis, such as sodium hydroxide, potassium hydroxide and/or lithium hydroxide, and/or the alkali metal oxides such, as sodium and/or potassium oxide or mixtures thereof. A preferred base is a caustic alkali, more preferably sodium hydroxide and/or potassium hydroxide.

Other suitable bases include ammonia, ammonium carbonate, all available carbonate salts such as $K_2CO_3$, $Na_2CO_3$, $CaCO_3$, $MgCO_3$, etc., alkanolamines (as e.g. monoethanolamine), urea and urea derivatives, polyamine, etc.

Typical levels of such bases, when present, are of from 0.01% to 5.0% by weight of the total composition, preferably from 0.05% to 3.0% and more preferably from 0.1% to 0.6%.

The compositions herein may comprise an acid to trim its pH to the required level, despite the presence of an acid, if any, the compositions herein will maintain their preferred neutral pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and a mixture thereof. A mixture of said acids may be commercially available from BASF under the trade name Sokalan® DCS. A suitable inorganic acid is selected from the group consisting hydrochloric acid, sulphuric acid, phosphoric acid and a mixture thereof.

A typical level of such an acid, when present, is of from 0.01% to 5.0% by weight of the total composition, preferably from 0.04% to 3.0% and more preferably from 0.05% to 1.5%.

In a preferred embodiment according to the present invention the compositions herein are thickened compositions. Preferably, the liquid compositions herein have a viscosity of up to 7500 cps at $20\ s^{-1}$, more preferably from 5000 cps to 50 cps, yet more preferably from 2000 cps to 50 cps and most preferably from 1500 cps to 300 cps at $20\ s^{-1}$ and 20° C. when measured with a Rheometer, model AR 1000 (Supplied by TA Instruments) with a 4 cm conic spindle in stainless steel, 2° angle (linear increment from 0.1 to 100 $sec^{-1}$ in max. 8 minutes).

In another preferred embodiment according to the present invention the compositions herein have a water-like viscosity. By "water-like viscosity" it is meant herein a viscosity that is close to that of water. Preferably the liquid compositions herein have a viscosity of up to 50 cps at 60 rpm, more preferably from 0 cps to 30 cps, yet more preferably from 0 cps to 20 cps and most preferably from 0 cps to 10 cps at 60 rpm and 20° C. when measured with a Brookfield digital viscometer model DV II, with spindle 2.

Biodegradable Abrasive Cleaning Particles

The liquid cleaning and/or cleansing composition herein comprise biodegradable abrasive cleaning particles that are selected or synthesized to feature effective shapes, e.g.: defined by circularity, solidity and adequate hardness.

By "biodegradable" it is meant herein chemical dissolution, disintegration or digestion of biodegradable abrasive particles in a compost media at a rate above 50% according to ASTM6400 test method. ASTM6400 test method refers to compostability of the material, but herein by compostability is meant biodegradability. The ultimate biodegradability of biodegradable abrasive particles under controlled composting conditions is determined in this test.

The biodegradable abrasive cleaning particles according to present invention have a biodegradability rate above 50% according to ASTM6400 test method, preferably a biodegradability rate above 60%, more preferably above 70% and yet more preferably above 80% and most preferably of 100% according to ASTM6400 test method.

Biodegradation is the chemical dissolution, disintegration or digestion of biodegradable abrasive particles in a compost media. Currently biodegradability is commonly associated with environmentally friendly products that are capable of decomposing back into natural elements. Organic material can be degraded aerobically with oxygen, or anaerobically without oxygen. Readily biodegradable materials discussed herein are material which biodegrade according to protocol and requirement described in ASTM6400 test method.

There are two main types of biodegradable plastics currently on the market: hydro-biodegradable plastics (HBP) and oxo-biodegradable plastics (OBP). Both will first undergo chemical degradation by hydrolysis and oxidation respectively. This results in their physical disintegration and a drastic reduction in their molecular weight. These smaller, lower molecular weight fragments are then amenable to biodegradation.

Hydro-biodegradable plastics are converted to carbon dioxide ($CO_2$), water ($H_2O$) and biomass, and they emit methane in anaerobic conditions.

Polyesters play a predominant role in hydro-biodegradable plastics due to their easily hydrolysable ester bonds upon microbial attack.

The biodegradable abrasive particles in the present invention comprise biodegradable material, preferably comprise aliphatic polyester. Aliphatic polyesters (I) are produced by catalyzed condensation reaction between aliphatic dicarboxylic acid (II) (or alternatively their anhydride form) or mixtures thereof and alkane diol (III) or mixtures thereof. Suitable number of carbon atoms for the present invention for dicarboxylic acid varies from 2 to 6 and number of carbon atoms in alkanediol varies from 2 to 4. Examples of suitable dicarboxylic acids for the present invention are oxalic acid, malonic acid, succinic acid, glutaric acid and adipic acid and mixtures thereof. Examples of suitable alkane diols are ethylene glycol, propanediol and butanediol and mixtures thereof.

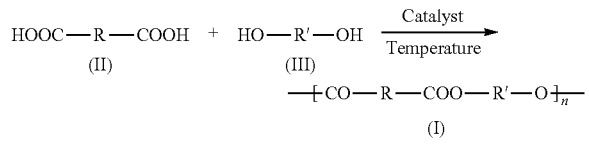

(I)

A suitable biodegradable aliphatic polyester for the present invention is polybutylene succinate (PBS) (IV). PBSs are a family of biodegradable polymers that can replace conventional thermoplastic used for packaging. PBS is biodegradable macromolecular polymer, which is synthesized from succinic acid and 1,4-butanediol through direct process of condensation polymerization

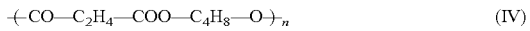 (IV)

Another suitable biodegradable aliphatic polyester for the present invention is polybutylene adipate (PBA) (V). PBA is biodegradable macromolecular polymer, which is synthesized from 1,4-butanediol and adipic acid through direct process of condensation polymerization.

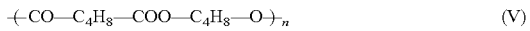 (V)

Another suitable biodegradable aliphatic polyester for the present invention is polybutylene succinate-co-polybutylene adipate (PBSA) (VI). PBSA is biodegradable macromolecular polymer which is synthesized from 1,4-butanediol and mixture of succinic acid and adipic acid through direct process of condensation polymerization.

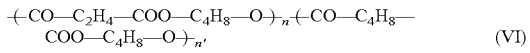 (VI)

Another suitable biodegradable aliphatic polyester for the present invention is polyethylene succinate (VII). Polyethylene succinate is biodegradable macromolecular polymer which is synthesized from ethylene glycol and succinic acid through direct process of condensation polymerization.

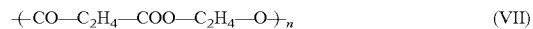 (VII)

Another suitable biodegradable aliphatic polyester for the present invention is polyethylene succinate-co-polyethylene adipate (VIII). Polyethylene succinate-co-polyethylene adipate is a biodegradable macromolecular polymer which is synthesized from ethylene glycol and mixture of succinic acid and adipic acid through a direct process of condensation polymerization.

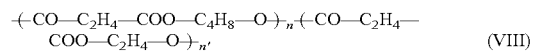 (VIII)

Another suitable biodegradable aliphatic polyester for the present invention is polypropylene succinate (IX). Polypropylene succinate is biodegradable macromolecular polymer which is synthesized from Propanediol and succinic acid through direct process of condensation polymerization.

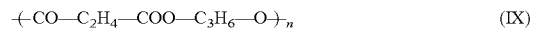 (IX)

Another suitable biodegradable aliphatic polyester for the present invention is polypropylene succinate-co-polypropylene adipate (X). Polypropylene succinate-co-polypropylene adipate is biodegradable macromolecular polymer which is synthesized from Propanediol and mixture of succinic acid and adipic acid through direct process of condensation polymerization.

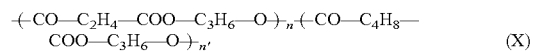 (X)

Preferably the molecular weight of these polymers varies from 10 to 3000 kDa.

Preferably the biodegradable abrasive particles comprise material selected from the group consisting of polybutylene succinate (PBS), polybutylene adipate (PBA), polybutylene succinate-co-polybutylene adipate (PBSA), polyethylene succinate, polyethylene succinate-co-polyethylene adipate, polypropylene succinate, polypropylene succinate-co-polypropylene adipate and mixtures thereof.

More preferably the biodegradable abrasive particles are made from the material selected from the group consisting PBS, PBA, PBSA and mixture thereof.

Most preferably the biodegradable abrasive particles comprise the material selected from the group consisting of PBS, PBSA and mixture thereof.

In a highly preferred embodiment, the biodegradable polymer is blended with abundant amount of mineral or vegetable (soluble or insoluble) filler. Such inclusion of a large quantity of filler help breaking the polymer into particles and feature biodegradable particle with large surface area e.g.: via porosity and capillarity which favor the degradation kinetics. This is especially the case when the filler is water soluble. Typical fillers to be used with PBS polymers are minerals e.g.: metal chloride e.g.: NaCl, KCl, etc, metal carbonate e.g.: $Na_2CO_3$, $NaHCO_3$, etc., metal sulfate e.g., $MgSO_4$, and generally all mineral adsorbents providing hardness is compatible with overall target hardness of the biodegradable abrasive cleaning particle. The filler can also be derived from vegetal feedstock essentially cellulose or lignocellulose based material e.g.: nut shell, wood or bamboo fibers, corn cob, rice hull, etc. including carbohydrate such starch such as flour, xanthan gum, alginic, dextran, agar, and the like. The suitable fillers are also biodegradable and do not change biodegradability of the final abrasive particles. Typically biodegradable polymer suitable for the present invention comprises filler from 10% to 70% by weight of the polymeric material, preferably from 20% to 60%, and most preferably from 40% to 50%.

Alternatively, polymeric fillers can also be blended to the biodegradable abrasive material in order to meet mechanical, rheological or hardness requirements. Typical polymeric fillers are also preferably biodegradable. Suitable polymeric fillers for the present invention can be selected from the group consisting of polyhydroxyalkanoates or polylactic acid, wherein quantities vary from 10% to 50% by weight of the polymeric material. Alternatively, non-biodegradable polymers can be used, although quantities in biodegradable abrasive material should not exceed 40% and preferably not exceed 20% in order to maintain sufficient biodegradable feature. Suitable non-biodegradable polymeric fillers can be selected or derived from the group consisting of polyethylene, polypropylene, polystyrene, PVC, polyacrylate, polyurethane and mixtures thereof.

In a preferred embodiment the biodegradable abrasive cleaning particles are preferably non-rolling. Additionally, in a preferred embodiment the biodegradable abrasive cleaning particles are preferably sharp.

The applicant has found that non-rolling and sharp biodegradable abrasive cleaning particles provide good soil removal and low surface damage. Indeed the applicant has found that very specific particle shapes e.g.: defined by circularity to promote effective sliding of the biodegradable abrasive particles vs. typical abrasive particles, where rolling movement is rather promoted and is less effective as displacing soil from the surface. The circularity to meet the criteria, to promote effective sliding of the particles is at range from 0.1 to 0.6.

The shape of the biodegradable abrasive cleaning particle can be defined in various ways. The present invention defines the cleaning particle shape in a form of particle, which reflects the geometrical proportions of a particle and more pragmatically of the particle population. Very recent analytical techniques allow an accurate simultaneous measurement of particle shapes from a large number of particles, typically greater than 10000 particles (preferably above 100 000). This enables accurate tuning and/or selection of average particle population shape with discriminative performance. These measurement analyses of particle shape are conducted using on Occhio Nano 500 Particle Characterisation Instrument with its accompanying software Callistro version 25 (Occhio s.a. Liege, Belgium). This instrument is used to prepare, disperse, image and analyse the particle samples, as per manufacturer's instructions, and the following instrument setting selections: White Requested=180, vacuum time=5000 ms, sedimentation time=5000 ms, automatic threshold, number of particles counted/analyses=8000 to 500000, minimum number of replicates/sample=3, lens setting 1×/1.5×.

The biodegradable abrasive cleaning particles of the present invention are defined by quantitative description of a shape. In quantitative description, shape descriptor is understood as numbers that can be calculated from particle images or physical particle properties via mathematical or numerical operations. While particle shape can be defined in 3-dimension with dedicated analytical technique, the applicant has found, that the characterization of the particles shape in 2-dimension is most relevant and correlates with the biodegradable abrasive performance of the cleaning particles. During the particle shape analysis protocol, the particles are orientated toward the surface—via gravity deposition—similarly to the expected particle orientation during the cleaning process. Hence, the object of the present invention regards the characterization of 2-D shape of a particle/particle population as defined by the projection of its shape on the surface on which the particle/particle population is deposited.

In a preferred embodiment, the biodegradable abrasive cleaning particles have a mean ECD from 10 μm to 1000 μm, preferably from 50 μm to 500 μm, more preferably from 100 μm to 350 μm and most preferably from 150 to 250 μm.

Indeed, the Applicant has found that the biodegradable abrasive cleaning particle size can be critical to achieve efficient cleaning performance whereas excessively biodegradable abrasive population with small particle sizes e.g.: typically below 10 micrometers feature polishing action vs. cleaning despite featuring a high number of particles per particle load in cleaner inherent to the small particle size. On the other hand, biodegradable abrasive population with excessively high particle size, e.g.: above 1000 micrometers, do not deliver optimal cleaning efficiency, because the number of particles per particle load in cleaner, decreases significantly inherently to the large particle size. Additionally, excessively small particle size are not desirable in cleaner/for cleaning task since in practice, small and numerous particles are often hard to remove from the various surface topologies which requires excessive effort to remove from the user unless leaving the surface with visible particles residue. On the other hand, excessively large particle are too easily detected visually or provide bad tactile experience while handling or using the cleaner. Therefore, the applicants define herein an optimal particle size range that delivers both optimal cleaning performance and usage experience.

The biodegradable abrasive cleaning particles have a size defined by their area-equivalent diameter (ISO 9276-6:2008 (E) section 7) also called Equivalent Circle Diameter ECD (ASTM F1877-05 Section 11.3.2). Mean ECD of particle population is calculated as the average of respective ECD of each particles of a particle population of at least 10 000 particles, preferably above 50 000 particles, more preferably above 100 000 particles after excluding from the measurement and calculation the data of particles having area-equivalent diameter (ECD) of below 10 micrometers. Mean data are extracted from volume-based vs. number-based measurements.

In one preferred example, the size of the biodegradable abrasive cleaning particles used in the present invention is altered during usage especially undergoing significant size reduction. Hence the particle remain visible or tactile detectable in liquid composition and in the beginning of the usage process to provide effective cleaning. As the cleaning process progresses, the biodegradable abrasive cleaning particles disperse or break into smaller particles and become invisible to an eye or tactile undetectable.

In the present invention shape descriptors are calculations of geometrical descriptors/shape factors. Geometrical shape factors are ratios between two different geometrical properties; such properties are usually a measure of proportions of the image of the whole particle or a measure of the proportions of an ideal geometrical body enveloping the particle or forms an envelope around the particle. These results are macroshape descriptors similar to aspect ratio, however the Applicant has discovered that mesoshape descriptors—a specific sub-class of macroshape descriptor—are particularly critical to the cleaning effectiveness and surface safety performances of the biodegradable abrasive cleaning particles, while more typical shape parameters such as aspect ratio has proved insufficient. These mesoshape descriptors describe how different a particle is compared to an ideal geometrical shape, especially how different compared to a sphere, and incidentally help define its ability for non-rolling, e.g.: sliding, effective cleaning movement pattern. The biodegradable abrasive cleaning particles of the present invention are different from typical spherical or spherical-resembling e.g.: granular, biodegradable abrasives forms.

The biodegradable abrasive cleaning particles of the present invention are non-spherical.

The non-spherical particles herein preferably have sharp edges and each particle has at least one edge or surface having concave curvature. More preferably, the non-spherical particles herein have a multitude of sharp edges and each particle has at least one edge or surface having concave curvature. The sharp edges of the non-spherical particles are defined by edge having a tip radius below 20 μm, preferably below 8 μm, most preferably below 5 μm. The tip radius is defined by the diameter of an imaginary circle fitting the curvature of the edge extremity.

FIG. 1 is an illustration of tip radius.

Circularity

Circularity is a quantitative, 2-dimension image analysis shape description and is being measured according to ISO 9276-6:2008(E) section 8.2 as implemented via the Occhio Nano 500 Particle Characterisation Instrument with its accompanying software Callistro version 25 (Occhio s.a. Liege, Belgium). Circularity is a preferred Mesoshape descriptor and is widely available in shape analysis instrument such as in Occhio Nano 500 or in Malvern Morphologi G3. Circularity is sometimes described in literature as being the difference between a particle's shape and a perfect sphere. Circularity values range from 0 to 1, where a circularity of 1 describes a perfectly spherical particles or disc particle as measured in a two dimensional image.

$$C = \sqrt{\frac{4\pi A}{P^2}}$$

Where A is projection area, which is 2D descriptor and P is the length of the perimeter of the particle.

The applicant has found out that the biodegradable abrasive cleaning particles having a mean circularity from 0.1 to 0.6, preferably from 0.15 to 0.4 and more preferably from 0.2 to 0.35 are providing improved cleaning performance and surface safety. Mean data are extracted from volume-based vs. number-based measurements.

Thus, in a preferred embodiment of the present invention the biodegradable abrasive cleaning particles herein have a mean circularity from 0.1 to 0.6, preferably from 0.15 to 0.4, and more preferably from 0.2 to 0.35.

Solidity

Solidity is a quantitative, 2-dimensional image analysis shape description, and is being measured according to ISO 9276-6:2008(E) section 8.2 as implemented via the Occhio Nano 500 Particle Characterisation Instrument with its accompanying software Callistro version 25 (Occhio s.a. Liege, Belgium). The non-spherical particle herein has preferably at least one edge or surface having a concave curvature. Solidity is a mesoshape parameter, which describes the overall concavity of a particle/particle population. Solidity values range from 0 to 1, where a solidity number of 1 describes a non-concave particle, as measured in literature as being:

Solidity=A/Ac

Where A is the area of the particle and Ac is the area of the convex hull (envelope) of bounding the particle.

The applicant has found out that the biodegradable abrasive cleaning particles having a mean solidity from 0.4 to 0.9, preferably solidity from 0.5 to 0.8 and more preferably from 0.55 to 0.65 are providing improved cleaning performance and surface safety. Mean data are extracted from volume-based vs. number-based measurements.

Thus, in a preferred embodiment of the present invention the biodegradable abrasive cleaning particles herein have a mean solidity from 0.4 to 0.9, preferably solidity from 0.5 to 0.8, and more preferably from 0.55 to 0.65.

Solidity is sometime also named Convexity in literature or in some apparatus software using the solidity formula in place of its definition described in ISO 9276-6 (convexity=Pc/P where P is the length of the perimeter of the particle and $P_C$ is length of the perimeter of the convex hull—envelope—bounding the particle). Despite solidity and convexity being similar mesoshape descriptor in concept, the applicants refer herein to the solidity measure expressed above by the Occhio Nano 500, as indicated above.

In highly preferred embodiment the biodegradable abrasive cleaning particles have a mean circularity from 0.1 to 0.6 (preferably from 0.15 to 0.4 and more preferably from 0.2 to 0.35) and mean solidity from 0.4 to 0.9 (preferably solidity from 0.5 to 0.8, and more preferably from 0.55 to 0.65).

By the term "mean circularity", "mean solidity" or "mean roughness", the applicant considers the average of the circularity or solidity or roughness values of each particle taken from a population of at least 10 000 particles, preferably above 50 000 particles, more preferably above 100 000 particles, after excluding from the measurement and calculation, the circularity or solidity or roughness data of particles having area-equivalent diameter (ECD) of below 10 micrometers. Mean data are extracted from volume-based vs. number-based measurements.

Typical shearing or graining methods to reduce the above material in biodegradable abrasive powder featuring useful shape defined by the targeted circularity range, so other preparation e.g.: grain shaping methods described in the art may be employed such as agglomerating, printing, carving, etc. Previous shaping processes are sometimes facilitated by mixing previous biodegradable abrasive materials as fillers within a thermoplastic or solidifying matrix. Such processes e.g.: including selection of matrix and respective load of filler are well known in art. A specifically preferred process to achieve particles matching effective circularity range consists at foaming the biodegradable abrasive raw material per se or biodegradable abrasive material dispersed within a matrix and reducing the achieved foam into biodegradable abrasive cleaning particles with improved efficiency. Foaming processes and foam structure are typically achieved via gas expansion process, e.g.: either by injecting gas or solvent within the biodegradable abrasive precursor and allowing expansion by pressure drop and/or increasing of temperature e.g.: extrusion foaming process or more conveniently with in-situ generated gas followed by hardening of the biodegradable abrasive precursor e.g.: polyurethane foaming process. Alternatively, foam structures can also be achieved via emulsion process, followed by hardening and drying step.

In a highly preferred embodiment herein, in order to achieve the geometrical shape descriptors of the biodegradable abrasive cleaning particles (i.e. circularity, solidity and/or roughness) the biodegradable abrasive cleaning particles are obtained from foamed polymeric material, which is reduced into the biodegradable abrasive cleaning particles preferably by grinding or milling as described herein later on.

The applicant has found that good cleaning efficiency will be achieved with the biodegradable abrasive cleaning particles, which have been made from a foam having density above 200 kg/m³, and even up to 500 kg/m³. However, the applicant has surprisingly found that significantly better cleaning effect can be achieved with the foam density being below 100 kg/m³, more preferably from 5 kg/m³ to 100 kg/m³ and most preferably from 25 kg/m³ to 50 kg/m³.

Similarly, the applicant has found that good cleaning efficiency can be achieved with biodegradable abrasive cleaning particles which have been made from the foams featuring close-cell structures; however, the applicant has surprisingly found that significantly better cleaning effect can be achieved with foam with open-cell structure.

Similarly, the applicant has found that good cleaning efficiency can be achieved the biodegradable abrasive cleaning particles which have been made from the foams featuring cell size ranging from 20 micrometers to 2000 micrometers. However the applicant has surprisingly found that significantly better cleaning effect can be achieved with the foam featuring cell size between 100-1000 micrometers, more preferably from 200 to 500 micrometers and most preferably from 300 to 450 micrometers. Foam cell size can be measured for instance using protocol described in ASTM D3576.

In a preferred embodiment, in order to favor the reduction of the foam into a particle, the foam has preferably sufficient brittleness, e.g.; upon stress, the foam has little tendency to deform but rather break into particles.

Efficient particles are then produced by accurately grinding the foam structure to target size and shape as described herein. Hence, for instance, when large particle size is desired, foam with large cell size is desirable and vice-et-versa. Additionally, in order to preserve an optimal particle shape while reducing the foam structure into a particle, it is recommended to not target particle size excessively below the dimension of the cell size of the foam. Typically, target particle size is not below about half of the foam cell size.

In order to favor the reduction of the foam into particles, the foam has preferably sufficient brittleness, e.g.: upon stress, the foam has little tendency to deform and is liable to fracture. This behavior may result if the polymer has a glass transition temperature significantly higher than the usage temperature or if the polymer has a high degree of crystallinity and the crystalline melting temperature is significantly above the usage temperature.

One suitable way of reducing the foam into the biodegradable abrasive cleaning particles herein is to grind or mill the foam. Other suitable means include the use of eroding tools such as a high speed eroding wheel with dust collector wherein the surface of the wheel is engraved with a pattern or is coated with abrasive sandpaper or the like to promote the foam to form the biodegradable abrasive cleaning particles herein.

Alternatively and in a highly preferred embodiment herein, the foam may be reduced to particles in several stages. First the bulk foam can be broken into pieces of a few cm dimensions by manually chopping or cutting, or using a mechanical tool such as a lumpbreaker, for example the Model 2036 from S Howes, Inc. of Silver Creek, N.Y.

Preferably the biodegradable abrasive cleaning particles obtained via grinding or milling operation are single particles, which do not have little remaining cell structure.

Incidentally, it has surprisingly been found that the biodegradable abrasive cleaning particles of the present invention show a good cleaning performance even at relatively low levels, such as preferably from 0.1% to 20%, preferably from 0.3% to 10%, more preferably from 0.5% to 5%, even more preferably from 1.0% to 3.0%, by weight of the total composition of said biodegradable abrasive cleaning particles.

In a preferred embodiment the biodegradable abrasive cleaning particles are obtained from a foam by reducing (preferably by grinding or milling) the foam into biodegradable abrasive cleaning particles. More preferably the biodegradable abrasive cleaning particles are obtained from foamed polymeric material, wherein polymeric material is selected from the group consisting of polybutylene succinate (PBS), polybutylene adipate (PBA), polybutylene succinate-co-polybutylene adipate (PBSA), polyethylene succinate, polyethylene succinate-co-polyethylene adipate, polypropylene succinate, polypropylene succinate-co-polypropylene adipate and mixtures thereof.

In highly preferred embodiment the biodegradable abrasive cleaning particles are obtained from a foam by reducing (preferably by grinding or milling) the foam, into biodegradable abrasive cleaning particles. More preferably the biodegradable abrasive cleaning particles are obtained from foamed polymeric material, wherein polymeric material is selected from the group consisting of polybutylene succinate, polybutylene succinate-co adipate and mixtures thereof.

The particles used in the present invention can be white, transparent or colored by use of suitable dyes and/or pigments. Additionally suitable color stabilizing agents can be used to stabilize desired color.

Hardness of the Biodegradable Abrasive Cleaning Particles:

Preferred biodegradable abrasive cleaning particles suitable for used herein are hard enough to provide good cleaning/cleansing performance, whilst providing a good surface safety profile.

The hardness of the biodegradable abrasive cleaning particles reduced from the foam can be modified by changing the raw material used to prepare the foam. The molecular composition of the aliphatic polyesters and copolymer itself, the mixture of different aliphatic polyesters especially the selection of aliphatic dicarboxylic acids or aliphatic diols having low molecular weight, the addition of suitable fillers and addition of compatible plasticizers are factors which have effect on the material hardness.

Preferred biodegradable abrasive cleaning particles in the present invention have hardness from 3 to 50 $kg/mm^2$, preferably from 4 to 25 $kg/mm^2$ and most preferably from 5 to 15 $kg/mm^2$ on the HV Vickers hardness.

Vickers Hardness Test Method:

Vickers hardness HV is measured at 23° C. according to standard methods ISO 14577-1, ISO 14577-2, ISO 14577-3. The Vickers hardness is measured from a solid block of the raw material at least 2 mm in thickness. The Vickers hardness micro indentation measurement is carried out by using the Micro-Hardness Tester (MHT), manufactured by CSM Instruments SA, Peseux, Switzerland.

As per the ISO 14577 instructions, the test surface should be flat and smooth, having a roughness (Ra) value less than 5% of the maximum indenter penetration depth. For a 200 μm maximum depth this equates to a Ra value less than 10 μm. As per ISO 14577, such a surface may be prepared by any suitable means, which may include cutting the block of test material with a new sharp microtome or scalpel blade, grinding, polishing or by casting melted material onto a flat, smooth casting form and allowing it to thoroughly solidify prior testing.

Suitable general settings for the Micro-Hardness Tester (MHT) are as follows:

Control mode: Displacement, Continuous
Maximum displacement: 200 μm
Approach speed: 20 nm/s
Zero point determination: at contact
Hold period to measure thermal drift at contact: 60 s
Force application time: 30 s
Frequency of data logging: at least every second
Hold time at maximum force: 30 s Force removal time: 30 s
Shape/Material of intender tip: Vickers Pyramid Shape/Diamond Tip Alternatively, the biodegradable abrasive cleaning particles in the present invention hardness may also expressed accordingly to the MOHS hardness scale. Preferably, the MOHS hardness is comprised between 0.5 and 3.5 and most preferably between 1 and 3. The MOHS hardness scale is an internationally recognized scale for measuring the hardness of a compound versus a compound of known hardness, see Encyclopedia of Chemical Technology, Kirk-Othmer, 4 th Edition Vol 1, page 18 or Lide, D. R (ed) CRC Handbook of Chemistry and Physics, 73 rd edition, Boca Raton, Fla.: The Rubber Company, 1992-1993. Many MOHS Test kits are commercially available containing material with known MOHS hardness. For measurement and selection of biodegradable abrasive material with selected MOHS hardness, it is recommended to execute the MOHS hardness measurement with un-shaped particles e.g.: with spherical or granular forms of the biodegradable abrasive material since MOHS measurement of shape particles will provide erroneous results.

The applicant has found that by choosing the biodegradable abrasive cleaning particles according to 2 dimensional shape parameters as described herein, biodegradable abrasive cleaning particles having a mean circularity from 0.1 to 0.4 and Vickers hardness from 3 kg/mm$^2$ to 50 kg/mm$^2$ and preferably a mean solidity from 0.4 to 0.75 and/or a mean roughness from 0.1 to 0.3 will provide good cleaning effectiveness and surface safety.

Optional Ingredients

The compositions according to the present invention may comprise a variety of optional ingredients depending on the technical benefit aimed for and the surface treated.

Suitable optional ingredients for use herein include chelating agents, surfactants, radical scavengers, perfumes, surface-modifying polymers, solvents, builders, buffers, bactericides, hydrotropes, colorants, stabilizers, bleaches, bleach activators, suds controlling agents like fatty acids, enzymes, soil suspenders, brighteners, anti dusting agents, dispersants, pigments, and dyes.

Suspending Aid

The biodegradable abrasive cleaning particles present in the composition herein are solid particles in a liquid composition. Said biodegradable abrasive cleaning particles may be suspended in the liquid composition. However, it is well within the scope of the present invention that such biodegradable abrasive cleaning particles are not-stably suspended within the composition and either settle or float on top of the composition. In this case, a user may have to temporally suspend the biodegradable abrasive cleaning particles by agitating (e.g., shaking or stirring) the composition prior to use.

However, it is preferred herein that the biodegradable abrasive cleaning particles are stably suspended in the liquid compositions herein. Thus the compositions herein comprise a suspending aid.

The suspending aid herein may either be a compound specifically chosen to provide a suspension of the biodegradable abrasive cleaning particles in the liquid compositions of the present invention, such as a structurant, or a compound that also provides another function, such as a thickener or a surfactant (as described herein elsewhere).

Any suitable organic and inorganic suspending aids typically used as gelling, thickening or suspending agents in cleaning/cleansing compositions and other detergent or cosmetic compositions may be used herein. Indeed, suitable organic suspending aids include polysaccharide polymers. In addition or as an alternative, polycarboxylate polymer thickeners may be used herein. Also, in addition or as an alternative of the above, layered silicate platelets e.g.: Hectorite, bentonite or montmorillonites can also be used. Suitable commercially available layered silicates are Laponite RD® or Optigel CL® available from Rockwood Additives. Suitable polycarboxylate polymer thickeners include (preferably lightly) crosslinked polyacrylate. A particularly suitable polycarboxylate polymer thickener is Carbopol commercially available from Lubrizol under the trade name Carbopol 674®.

Suitable polysaccharide polymers for use herein include substituted cellulose materials like carboxymethylcellulose, ethyl cellulose, hydroxyethyl cellulose, hydroxypropyl cellulose, hydroxymethyl cellulose, succinoglycan and naturally occurring polysaccharide polymers like Xanthan gum, gellan gum, guar gum, locust bean gum, tragacanth gum, succinoglucan gum, or derivatives thereof, or mixtures thereof. Xanthan gum is commercially available from Kelco under the tradename Kelzan T.

Preferably the suspending aid herein is Xanthan gum. In an alternative embodiment, the suspending aid herein is a polycarboxylate polymer thickeners preferably a (preferably lightly) crosslinked polyacrylate. In a highly preferred embodiment herein, the liquid compositions comprise a combination of a polysaccharide polymer or a mixture thereof, preferably Xanthan gum, with a polycarboxylate polymer or a mixture thereof, preferably a crosslinked polyacrylate.

As a preferred example, Xanthan gum is preferably present at levels between 0.1% to 5% by weight of the total composition, more preferably from 0.5% to 2%, even more preferably from 0.8% to 1.2%.

Organic Solvent

As an optional but highly preferred ingredient the composition herein comprises an organic solvents or mixtures thereof.

The compositions herein comprise from 0% to 30% by weight of the total composition of an organic solvent or a mixture thereof, more preferably 1.0% to 20% and most preferably, 2% to 15%.

Suitable solvents can be selected from the group consisting of: aliphatic alcohols, ethers and diethers having from 4 to 14 carbon atoms, preferably from 6 to 12 carbon atoms, and more preferably from 8 to 10 carbon atoms; glycols or alkoxylated glycols; glycol ethers; alkoxylated aromatic alcohols; aromatic alcohols; terpenes; and mixtures thereof. Aliphatic alcohols and glycol ether solvents are most preferred.

Aliphatic alcohols, of the formula R—OH wherein R is a linear or branched, saturated or unsaturated alkyl group of from 1 to 20 carbon atoms, preferably from 2 to 15 and more preferably from 5 to 12, are suitable solvents. Suitable aliphatic alcohols are methanol, ethanol, propanol, isopropanol or mixtures thereof. Among aliphatic alcohols, ethanol and isopropanol are most preferred because of their high vapour pressure and tendency to leave no residue.

Suitable glycols to be used herein are according to the formula HO—CR$_1$R$_2$—OH wherein R1 and R2 are independently H or a C$_2$-C$_{10}$ saturated or unsaturated aliphatic hydrocarbon chain and/or cyclic. Suitable glycols to be used herein are dodecaneglycol and/or propanediol.

In one preferred embodiment, at least one glycol ether solvent is incorporated in the compositions of the present invention. Particularly preferred glycol ethers have a terminal C$_3$-C$_6$ hydrocarbon attached to from one to three ethylene glycol or propylene glycol moieties to provide the appropriate degree of hydrophobicity and, preferably, surface activity. Examples of commercially available solvents based on ethylene glycol chemistry include mono-ethylene glycol n-hexyl ether (Hexyl Cellosolve®) available from Dow Chemical. Examples of commercially available solvents based on propylene glycol chemistry include the di-, and tri-propylene glycol derivatives of propyl and butyl alcohol, which are available from Arco under the trade names Arcosolv® and Dowanol®.

In the context of the present invention, preferred solvents are selected from the group consisting of mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, and mixtures thereof. "Butyl" includes normal butyl, isobutyl and tertiary butyl groups. Mono-propylene glycol and mono-propylene glycol mono-butyl ether are the most preferred cleaning solvent and are available under the tradenames Dowanol DPnP® and Dowanol DPnB®. Di-propylene glycol mono-t-butyl ether is commercially available from Arco Chemical under the tradename Arcosolv PTB®.

In a particularly preferred embodiment, the cleaning solvent is purified so as to minimize impurities. Such impurities include aldehydes, dimers, trimers, oligomers and other by-products. These have been found to deleteriously affect product odor, perfume solubility and end result. The inventors have also found that common commercial solvents, which contain low levels of aldehydes, can cause irreversible and irreparable yellowing of certain surfaces. By purifying the cleaning solvents so as to minimize or eliminate such impurities, surface damage is attenuated or eliminated.

Though not preferred, terpenes can be used in the present invention. Suitable terpenes to be used herein monocyclic terpenes, dicyclic terpenes and/or acyclic terpenes. Suitable terpenes are: D-limonene; pinene; pine oil; terpinene; terpene derivatives as menthol, terpineol, geraniol, thymol; and the citronella or citronellol types of ingredients.

Suitable alkoxylated aromatic alcohols to be used herein are according to the formula $R-(A)_n-OH$ wherein R is an alkyl substituted or non-alkyl substituted aryl group of from 1 to 20 carbon atoms, preferably from 2 to 15 and more preferably from 2 to 10, wherein A is an alkoxy group preferably butoxy, propoxy and/or ethoxy, and n is an integer of from 1 to 5, preferably 1 to 2. Suitable alkoxylated aromatic alcohols are benzoxyethanol and/or benzoxypropanol.

Suitable aromatic alcohols to be used herein are according to the formula R—OH wherein R is an alkyl substituted or non-alkyl substituted aryl group of from 1 to 20 carbon atoms, preferably from 1 to 15 and more preferably from 1 to 10. For example a suitable aromatic alcohol to be used herein is benzyl alcohol.

Surfactants

The compositions herein may comprise a nonionic, anionic, zwitterionic, cationic and amphoteric surfactant or mixtures thereof. Suitable surfactants are those selected from the group consisting of nonionic, anionic, zwitterionic, cationic and amphoteric surfactants, having hydrophobic chains containing from 8 to 18 carbon atoms. Examples of suitable surfactants are described in McCutcheon's Vol. 1: Emulsifiers and Detergents, North American Ed., McCutcheon Division, MC Publishing Co., 2002.

Preferably, the composition herein comprises from 0.01% to 20% by weight of the total composition of a surfactant or a mixture thereof, more preferably from 0.5% to 10%, and most preferably from 1% to 5%.

Non-ionic surfactants are highly preferred for use in the compositions of the present invention. Non-limiting examples of suitable non-ionic surfactants include alcohol alkoxylates, alkyl polysaccharides, amine oxides, block copolymers of ethylene oxide and propylene oxide, fluoro surfactants and silicon based surfactants. Preferably, the aqueous compositions comprise from 0.01% to 20% by weight of the total composition of a non-ionic surfactant or a mixture thereof, more preferably from 0.5% to 10%, and most preferably from 1% to 5%.

A preferred class of non-ionic surfactants suitable for the present invention is alkyl ethoxylates. The alkyl ethoxylates of the present invention are either linear or branched, and contain from 8 carbon atoms to 16 carbon atoms in the hydrophobic tail, and from 3 ethylene oxide units to 25 ethylene oxide units in the hydrophilic head group. Examples of alkyl ethoxylates include Neodol 91-6®, Neodol 91-8® supplied by the Shell Corporation (P.O. Box 2463, 1 Shell Plaza, Houston, Tex.), and Alfonic 810-60® supplied by Condea Corporation, (900 Threadneedle P.O. Box 19029, Houston, Tex.). More preferred alkyl ethoxylates comprise from 9 to 12 carbon atoms in the hydrophobic tail, and from 4 to 9 oxide units in the hydrophilic head group. A most preferred alkyl ethoxylate is $C_{9-11}$ $EO_5$, available from the Shell Chemical Company under the tradename Neodol 91-5®. Non-ionic ethoxylates can also be derived from branched alcohols. For example, alcohols can be made from branched olefin feedstocks such as propylene or butylene. In a preferred embodiment, the branched alcohol is either a 2-propyl-1-heptyl alcohol or 2-butyl-1-octyl alcohol. A desirable branched alcohol ethoxylate is 2-propyl-1-heptyl EO7/AO7, manufactured and sold by BASF Corporation under the tradename Lutensol XP 79/XL 79®.

Another class of non-ionic surfactant suitable for the present invention is alkyl polysaccharides. Such surfactants are disclosed in U.S. Pat. Nos. 4,565,647, 5,776,872, 5,883, 062, and 5,906,973. Among alkyl polysaccharides, alkyl polyglycosides comprising five and/or six carbon sugar rings are preferred, those comprising six carbon sugar rings are more preferred, and those wherein the six carbon sugar ring is derived from glucose, i.e., alkyl polyglucosides ("APG"), are most preferred. The alkyl substituent in the APG chain length is preferably a saturated or unsaturated alkyl moiety containing from 8 to 16 carbon atoms, with an average chain length of 10 carbon atoms. $C_8$-$C_{16}$ alkyl polyglucosides are commercially available from several suppliers (e.g., Simusol® surfactants from Seppic Corporation, 75 Quai d'Orsay, 75321 Paris, Cedex 7, France, and Glucopon 220®, Glucopon 225®, Glucopon 425®, Plantaren 2000 N®, and Plantaren 2000 N UP®, from Cognis Corporation, Postfach 13 01 64, D 40551, Dusseldorf, Germany).

Another class of non-ionic surfactant suitable for the present invention is amine oxide. Amine oxides, particularly those comprising from 10 carbon atoms to 16 carbon atoms in the hydrophobic tail, are beneficial because of their strong cleaning profile and effectiveness even at levels below 0.10%. Additionally $C_{10-16}$ amine oxides, especially $C_{12}$-$C_{14}$ amine oxides are excellent solubilizers of perfume. Alternative non-ionic detergent surfactants for use herein are alkoxylated alcohols generally comprising from 8 to 16 carbon atoms in the hydrophobic alkyl chain of the alcohol. Typical alkoxylation groups are propoxy groups or ethoxy groups in combination with propoxy groups, yielding alkyl ethoxy propoxylates. Such compounds are commercially available under the tradename Antarox® available from Rhodia (40

Rue de la Haie-Coq F-93306, Aubervilliers Cédex, France) and under the tradename Nonidet® available from Shell Chemical.

The condensation products of ethylene oxide with a hydrophobic base formed by the condensation of propylene oxide with propylene glycol are also suitable for use herein. The hydrophobic portion of these compounds will preferably have a molecular weight of from 1500 to 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to 40 moles of ethylene oxide. Examples of compounds of this type include certain of the commercially available Pluronic® surfactants, marketed by BASF. Chemically, such surfactants have the structure $(EO)_x(PO)_y(EO)_z$ or $(PO)_x(EO)_y(PO)_z$ wherein x, y, and z are from 1 to 100, preferably 3 to 50. Pluronic® surfactants known to be good wetting surfactants are more preferred. A description of the Pluronic® surfactants, and properties thereof, including wetting properties, can be found in the brochure entitled "BASF Performance Chemicals Plutonic® & Tetronic® Surfactants", available from BASF.

Other suitable though not preferred non-ionic surfactants include the polyethylene oxide condensates of alkyl phenols, e.g., the condensation products of alkyl phenols having an alkyl group containing from 6 to 12 carbon atoms in either a straight chain or branched chain configuration, with ethylene oxide, the said ethylene oxide being present in amounts equal to 5 to 25 moles of ethylene oxide per mole of alkyl phenol. The alkyl substituent in such compounds can be derived from oligomerized propylene, diisobutylene, or from other sources of iso-octane n-octane, iso-nonane or n-nonane. Other non-ionic surfactants that can be used include those derived from natural sources such as sugars and include $C_8$-$C_{16}$ N-alkyl glucose amide surfactants.

Suitable anionic surfactants for use herein are all those commonly known by those skilled in the art. Preferably, the anionic surfactants for use herein include alkyl sulphonates, alkyl aryl sulphonates, alkyl sulphates, alkyl alkoxylated sulphates, $C_6$-$C_{20}$ alkyl alkoxylated linear or branched diphenyl oxide disulphonates, or mixtures thereof.

Suitable alkyl sulphonates for use herein include water-soluble salts or acids of the formula $RSO_3M$ wherein R is a $C_6$-$C_{20}$ linear or branched, saturated or unsaturated alkyl group, preferably a $C_8$-$C_{18}$ alkyl group and more preferably a $C_{10}$-$C_{16}$ alkyl group, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like).

Suitable alkyl aryl sulphonates for use herein include water-soluble salts or acids of the formula $RSO_3M$ wherein R is an aryl, preferably a benzyl, substituted by a $C_6$-$C_{20}$ linear or branched saturated or unsaturated alkyl group, preferably a $C_8$-$C_{18}$ alkyl group and more preferably a $C_{10}$-$C_{16}$ alkyl group, and M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like).

An example of a $C_{14}$-$C_{16}$ alkyl sulphonate is Hostapur® SAS available from Hoechst. An example of commercially available alkyl aryl sulphonate is Lauryl aryl sulphonate from Su.Ma. Particularly preferred alkyl aryl sulphonates are alkyl benzene sulphonates commercially available under trade name Nansa® available from Albright&Wilson.

Suitable alkyl sulphate surfactants for use herein are according to the formula $R_1SO_4M$ wherein $R_1$ represents a hydrocarbon group selected from the group consisting of straight or branched alkyl radicals containing from 6 to 20 carbon atoms and alkyl phenyl radicals containing from 6 to 18 carbon atoms in the alkyl group. M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like).

Particularly preferred branched alkyl sulphates to be used herein are those containing from 10 to 14 total carbon atoms like Isalchem 123 AS®. Isalchem 123 AS® commercially available from Enichem is a $C_{12-13}$ surfactant which is 94% branched. This material can be described as $CH_3$—$(CH_2)_m$—$CH(CH_2OSO_3Na)$—$(CH_1)_n$—$CH_3$ where n+m=8-9. Also preferred alkyl sulphates are the alkyl sulphates where the alkyl chain comprises a total of 12 carbon atoms, i.e., sodium 2-butyl octyl sulphate. Such alkyl sulphate is commercially available from Condea under the trade name Isofol® 12 S. Particularly suitable liner alkyl sulphonates include $C_{12}$-$C_{16}$ paraffin sulphonate like Hostapur® SAS commercially available from Hoechst.

Suitable alkyl alkoxylated sulphate surfactants for use herein are according to the formula $RO(A)_mSO_3M$ wherein R is an unsubstituted $C_6$-$C_{20}$ alkyl or hydroxyalkyl group having a $C_6$-$C_{20}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy unit, m is greater than zero, typically between 0.5 and 6, more preferably between 0.5 and 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperidinium and cations derived from alkanolamines such as ethylamine, diethylamine, triethylamine, mixtures thereof, and the like. Exemplary surfactants are $C_{12}$-$C_{18}$ alkyl polyethoxylate (1.0) sulfate ($C_{12}$-$C_{18}E(1.0)SM$), $C_{12}$-$C_{18}$ alkyl polyethoxylate (2.25) sulfate ($C_{12}$-$C_{18}E(2.25)SM$), $C_{12}$-$C_{18}$ alkyl polyethoxylate (3.0) sulfate ($C_{12}$-$C_{18}E(3.0)SM$), $C_{12}$-$C_{18}$ alkyl polyethoxylate (4.0) sulfate ($C_{12}$-$C_{18}E(4.0)SM$), wherein M is conveniently selected from sodium and potassium.

Suitable $C_6$-$C_{20}$ alkyl alkoxylated linear or branched diphenyl oxide disulphonate surfactants for use herein are according to the following formula:

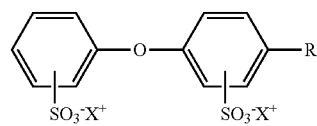

wherein R is a $C_6$-$C_{20}$ linear or branched, saturated or unsaturated alkyl group, preferably a $C_{12}$-$C_{18}$ alkyl group and more preferably a $C_{14}$-$C_{16}$ alkyl group, and X+ is H or a cation, e.g., an alkali metal cation (e.g., sodium, potassium, lithium, calcium, magnesium and the like). Particularly suitable $C_6$-$C_{20}$ alkyl alkoxylated linear or branched diphenyl oxide disulphonate surfactants to be used herein are the $C_{12}$ branched diphenyl oxide disulphonic acid and $C_{16}$ linear diphenyl oxide disulphonate sodium salt respectively commercially available by DOW under the trade name Dowfax 2A1® and Dowfax 8390®.

Other anionic surfactants useful herein include salts (including, for example, sodium, potassium, ammonium, and substituted ammonium salts such as mono-, di- and triethanolamine salts) of soap, $C_8$-$C_{24}$ olefinsulfonates, sulphonated polycarboxylic acids prepared by sulphonation of the pyrolyzed product of alkaline earth metal citrates, e.g., as described in British patent specification No. 1,082,179, $C_8$-$C_{24}$ alkylpolyglycolethersulfates (containing up to 10 moles of ethylene oxide); alkyl ester sulfonates such as $C_{14}$-$C_{16}$ methyl ester sulfonates; acyl glycerol sulfonates, fatty oleyl glycerol sulfates, alkyl phenol ethylene oxide ether sulfates, alkyl phosphates, isethionates such as the acyl isethionates, N-acyl taurates, alkyl succinamates and sulfosuccinates, monoesters of sulfosuccinate (especially saturated and unsaturated $C_{12}$-$C_{18}$ monoesters) diesters of sulfosuccinate (especially saturated and unsaturated $C_6$-$C_{14}$ diesters), acyl sarcosinates, sulfates of alkylpolysaccharides such as the sulfates of alkylpolyglucoside (the nonionic nonsulfated compounds being described below), alkyl polyethoxy carboxylates such as those of the formula $RO(CH_2CH_2O)_k CH_2COO^-M^+$ wherein R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Zwitterionic surfactants represent another class of preferred surfactants within the context of the present invention.

Zwitterionic surfactants contain both cationic and anionic groups on the same molecule over a wide pH range. The typical cationic group is a quaternary ammonium group, although other positively charged groups like sulfonium and phosphonium groups can also be used. The typical anionic groups are carboxylates and sulfonates, preferably sulfonates, although other groups like sulfates, phosphates and the like, can be used. Some common examples of these detergents are described in the patent literature: U.S. Pat. Nos. 2,082,275, 2,702,279 and 2,255,082.

A specific example of a zwitterionic surfactant is 3-(N-dodecyl-N,N-dimethyl)-2-hydroxypropane-1-sulfonate (Lauryl hydroxyl sultaine) available from the McIntyre Company (24601 Governors Highway, University Park, Ill. 60466, USA) under the tradename Mackam LHS®. Another specific zwitterionic surfactant is $C_{12-14}$ acylamidopropylene (hydroxypropylene) sulfobetaine that is available from McIntyre under the tradename Mackam 50-SB®. Other very useful zwitterionic surfactants include hydrocarbyl, e.g., fatty alkylene betaines. A highly preferred zwitterionic surfactant is Empigen BB®, a coco dimethyl betaine produced by Albright & Wilson. Another equally preferred zwitterionic surfactant is Mackam 35HP®, a coco amido propyl betaine produced by McIntyre.

Another class of preferred surfactants comprises the group consisting of amphoteric surfactants. One suitable amphoteric surfactant is a $C_8$-$C_{16}$ amido alkylene glycinate surfactant ('ampho glycinate'). Another suitable amphoteric surfactant is a $C_8$-$C_{16}$ amido alkylene propionate surfactant ('ampho propionate'). Other suitable, amphoteric surfactants are represented by surfactants such as dodecylbeta-alanine, N-alkyltaurines such as the one prepared by reacting dodecylamine with sodium isethionate according to the teaching of U.S. Pat. No. 2,658,072, N-higher alkylaspartic acids such as those produced according to the teaching of U.S. Pat. No. 2,438,091, and the products sold under the trade name "Miranol®", and described in U.S. Pat. No. 2,528,378.

Chelating Agents

One class of optional compounds for use herein includes chelating agents or mixtures thereof. Chelating agents can be incorporated in the compositions herein in amounts ranging from 0.0% to 10.0% by weight of the total composition, preferably from 0.01% to 5.0%.

Suitable phosphonate chelating agents for use herein may include alkali metal ethane 1-hydroxy diphosphonates (HEDP), alkylene poly (alkylene phosphonate), as well as amino phosphonate compounds, including amino aminotri (methylene phosphonic acid) (ATMP), nitrilo trimethylene phosphonates (NTP), ethylene diamine tetra methylene phosphonates, and diethylene triamine penta methylene phosphonates (DTPMP). The phosphonate compounds may be present either in their acid form or as salts of different cations on some or all of their acid functionalities. Preferred phosphonate chelating agents to be used herein are diethylene triamine penta methylene phosphonate (DTPMP) and ethane 1-hydroxy diphosphonate (HEDP). Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins. Ethylenediamine N,N'-disuccinic acids is, for instance, commercially available under the tradename ssEDDS® from Palmer Research Laboratories.

Suitable amino carboxylates for use herein include ethylene diamine tetra acetates, diethylene triamine pentaacetates, diethylene triamine pentaacetate (DTPA), N-hydroxyethylethylenediamine triacetates, nitrilotri-acetates, ethylenediamine tetrapropionates, triethylenetetraaminehexa-acetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are diethylene triamine penta acetic acid, propylene diamine tetracetic acid (PDTA) which is, for instance, commercially available from BASF under the trade name Trilon FS® and methyl glycine di-acetic acid (MGDA).

Further carboxylate chelating agents for use herein include salicylic acid, aspartic acid, glutamic acid, glycine, malonic acid or mixtures thereof.

Radical Scavenger

The compositions of the present invention may further comprise a radical scavenger or a mixture thereof.

Suitable radical scavengers for use herein include the well-known substituted mono and dihydroxy benzenes and their analogs, alkyl and aryl carboxylates and mixtures thereof. Preferred such radical scavengers for use herein include di-tert-butyl hydroxy toluene (BHT), hydroquinone, di-tert-butyl hydroquinone, mono-tert-butyl hydroquinone, tert-butylhydroxy anysole, benzoic acid, toluic acid, catechol, t-butyl catechol, benzylamine, 1,1,3-tris(2-methyl-4-hydroxy-5-t-butylphenyl) butane, n-propyl-gallate or mixtures thereof and highly preferred is di-tert-butyl hydroxy toluene. Such radical scavengers like N-propyl-gallate may be commercially available from Nipa Laboratories under the trade name Nipanox S1®.

Radical scavengers, when used, may be typically present herein in amounts up to 10% by weight of the total composition and preferably from 0.001% to 0.5% by weight. The presence of radical scavengers may contribute to the chemical stability of the compositions of the present invention.

Perfume

Suitable perfume compounds and compositions for use herein are for example those described in EP-A-0 957 156 under the paragraph entitled "Perfume", on page 13. The compositions herein may comprise a perfume ingredient, or mixtures thereof, in amounts up to 5.0% by weight of the total composition, preferably in amounts of from 0.1% to 1.5%.

Dye

The liquid compositions according to the present invention may be coloured. Accordingly, they may comprise a dye or a mixture thereof.

Delivery Form of the Compositions

The compositions herein may be packaged in a variety of suitable packaging known to those skilled in the art, such as plastic bottles for pouring liquid compositions, squeeze bottles or bottles equipped with a trigger sprayer for spraying liquid compositions. Alternatively, the paste-like compositions according to the present invention may by packed in a tube.

In an alternative embodiment herein, the liquid composition herein is impregnated onto a substrate; preferably the substrate is in the form of a flexible, thin sheet or a block of material, such as a sponge.

Suitable substrates are woven or non-woven sheets, cellulosic material based sheets, sponge or foam with open cell structures e.g.: polyurethane foams, cellulosic foam, melamine foam, etc.

The Process of Cleaning a Surface

The present invention encompasses a process of cleaning and/or cleansing a surface with a liquid composition according to the present invention. Suitable surfaces herein are described herein above under the heading "The liquid cleaning/cleansing composition".

In a preferred embodiment said surface is contacted with the composition according to the present invention, preferably wherein said composition is applied onto said surface.

In another preferred embodiment, the process herein comprises the steps of dispensing (e.g., by spraying, pouring, squeezing) the liquid composition according to the present invention from a container containing said liquid composition and thereafter cleaning and/or cleansing said surface.

The composition herein may be in its neat form or in its diluted form.

By "in its neat form", it is to be understood that said liquid composition is applied directly onto the surface to be treated without undergoing any dilution, i.e., the liquid composition herein is applied onto the surface as described herein.

By "diluted form", it is meant herein that said liquid composition is diluted by the user typically with water. The liquid composition is diluted prior to use to a typical dilution level of up to 10 times its weight of water. A usually recommended dilution level is a 10% dilution of the composition in water.

The composition herein may be applied using an appropriate implement, such as a mop, paper towel, brush (e.g., a toothbrush) or a cloth, soaked in the diluted or neat composition herein. Furthermore, once applied onto said surface said composition may be agitated over said surface using an appropriate implement. Indeed, said surface may be wiped using a mop, paper towel, brush or a cloth.

The process herein may additionally contain a rinsing step, preferably after the application of said composition. By "rinsing", it is meant herein contacting the surface cleaned/cleansed with the process according to the present invention with substantial quantities of appropriate solvent, typically water, directly after the step of applying the liquid composition herein onto said surface. By "substantial quantities", it is meant herein between 0.01 lt. and 1 lt. of water per $m^2$ of surface, more preferably between 0.1 lt. and 1 lt. of water per $m^2$ of surface.

Preferred embodiment herein, process of cleaning/cleansing is a process of cleaning household hard surfaces with a liquid composition according to present invention.

EXAMPLES

These following compositions were made comprising the listed ingredients in the listed proportions (weight %). Examples 1-37 herein are met to exemplify the present invention but are not necessarily used to limit or otherwise define the scope of the present invention.

Abrasive particle used in the examples below were ground from rigid polybutylene succinate foam (controlled foam structure e.g.: foam density, cell size, strut aspect ratio and % closed cell content).

Hard Surface Cleaner Bathroom Composition:

| % Weight | 1 | 2 | 3 |
| --- | --- | --- | --- |
| C9-C11 EO8 (Neodol 91-8 ®) | 3 | 2.5 | 3.5 |
| Alkyl Benzene sulfonate | | 1 | |
| C12-14-dimethyl Aminoxide | | 1 | |
| n-Butoxy Propoxy Propanol | | 2 | 2.5 |
| Hydrogene Peroxide | 3 | | |
| Hydrophobic ethoxylated polyurethane (Acusol 882 ®) | 1.5 | 1 | 0.8 |
| Lactic Acid | 3 | | 3.5 |
| Citric Acid | | 3 | 0.5 |
| Polysaccharide (Xanthan Gum, Keltrol CG-SFT ® Kelco) | 0.25 | 0.25 | 0.25 |
| Perfume | 0.35 | 0.35 | 0.35 |
| Biodegradable abrasive cleaning particles obtained from PBS foam | 1 | 1 | 1 |
| Water | Balance | Balance | Balance |

Hard Surface Cleaner Bathroom Composition (Cont.):

| % Weight | 4 | 5 | 6 |
| --- | --- | --- | --- |
| Chloridric acid | 2 | | |
| Linear C10 alkyl sulphate | 1.3 | 2 | 3 |
| n-Butoxy Propoxy Propanol | 2 | | 1.75 |
| Citric Acid | | 3 | 3 |
| PolyvinylPyrrolidone (Luviskol K60 ®) | 0.1 | 0.1 | 0.1 |
| NaOH | | 0.2 | 0.2 |
| Perfume | 0.4 | 0.4 | 0.4 |
| Polysaccharide (Xanthan Gum Kelzan T ®, Kelco) | 0.3 | 0.35 | 0.35 |
| Biodegradable abrasive cleaning particles obtained from PBS foam | 2 | 2 | 2 |
| Water | Balance | Balance | Balance |

Hand-Dishwashing Detergent Compositions:

| % Weight | 7 | 8 | 9 |
|---|---|---|---|
| N-2-ethylhexyl sulfocuccinamate | 3 | 3 | 3 |
| C11EO5 | 7 | 14 | |
| C11-EO7 | | | 7 |
| C10-EO7 | 7 | | 7 |
| Trisodium Citrate | 1 | 1 | 1 |
| Potassium Carbonate | 0.2 | 0.2 | 0.2 |
| Perfume | 1 | 1 | 1 |
| Polysaccharide (Xanthan Gum Kelzan T ®, Kelco) | 0.35 | 0.35 | 0.35 |
| Biodegradable abrasive cleaning particles obtained from PBS foam | 2 | 2 | 2 |
| Water (+ minor e.g.; pH adjusted to 10.5) | Balance | Balance | Balance |

General Degreaser Composition:

| % Weight | 10 | 11 |
|---|---|---|
| C9-C11 EO8 (Neodol 91-8 ®) | 3 | 3 |
| N-Butoxy Propoxy Propanol | 15 | 15 |
| Ethanol | 10 | 5 |
| Isopropanol | | 10 |
| Polysaccharide (Xanthan Gum-glyoxal modified Optixan-T) | 0.35 | 0.35 |
| Biodegradable abrasive cleaning particles obtained from PBS foam | 1 | 1 |
| Water (+ minor e.g.; pH adjusted to alkaline pH) | Balance | Balance |

Scouring Composition:

| % Weight | 12 | 13 | 14 |
|---|---|---|---|
| Sodium C13-16 prafin sulfonate | 2.5 | 2.5 | 2.5 |
| C12-14-EO7 (Lutensol AO7 ®) | 0.5 | 0.5 | 0.5 |
| Coconut Fatty Acid | 0.3 | 0.3 | 0.3 |
| Sodium Citrate | 3.3 | 3.3 | 3.3 |
| Sodium Carbonate | 3 | 3 | 3 |
| Orange terpenes | 2.1 | 2.1 | 2.1 |
| Benzyl Alcohol | 1.5 | 1.5 | |
| Polyacrylic acid 1.5 Mw | 0.75 | 0.75 | 0.75 |
| Diatomaceous earth (Celite 499 ® median size 10 μm) | 25 | | |
| Calcium Carbonate (Merk 2066 ® median size 10 μm) | | 25 | |
| Biodegradable abrasive cleaning particles obtained from PBS foam | 5 | 5 | 5 |
| Water | Balance | Balance | Balance |

Liquid Glass Cleaner:

| % Weight | 15 | 16 |
|---|---|---|
| Butoxypropanol | 2 | 4 |
| Ethanol | 3 | 6 |
| C12-14 sodium sulphate | 0.24 | |
| NaOH/Citric acid | To pH 10 | |
| Citric Acid | | |
| Biodegradable abrasive cleaning particles obtained from polybutylene succinate foam | 0.5 | 0.5 |
| Water (+ minor) | Balance | Balance |

Oral Care Composition (Toothpaste):

| % Weight | 20 | 21 |
|---|---|---|
| Sorbitol (70% sol.) | 24.2 | 24.2 |
| Glycerin | 7 | 7 |
| Carboxymethylcellulose | 0.5 | 0.5 |
| PEG-6 | 4 | 4 |
| Sodium Fluoride | 0.24 | 0.24 |
| Sodium Saccharine | 0.13 | 0.13 |
| Mono Sodium phosphate | 0.41 | 0.41 |
| Tri Sodium phosphate | 0.39 | 0.39 |
| Sodium Tartrate | 1 | 1 |
| TiO2 | 0.5 | 0.5 |
| Silica | 35 | |
| Sodium lauroyl sarcosinate (95% active) | 1 | 1 |
| Flavor | 0.8 | 0.8 |
| Biodegradable abrasive cleaning particles obtained from PBS foam | 2 | 5 |
| Water | Balance | Balance |

Examples 22 to 26 are made the following way:

Add Carbopol® to de-ionized free water of the formulation. Add all surfactants except cationics and betaines. If the pH is less than 6 then add a neutralizing agent (typically a base i.e., Triethanolamine, sodium hydroxide) to adjust to a pH greater than 6. If necessary, apply gentle heat to reduce viscosity and help minimize air entrapment. Add betaine and/or cationic surfactants. Add conditioning agents, additional rheology modifiers, pearlizing agents, encapsulated materials, exfoliants, preservatives, dyes, fragrances, abrasive particles and other desirable ingredients. Lastly, if desired reduce the pH with an acid (i.e. citric acid) and increase viscosity by adding sodium chloride.

Oral Care Composition (Toothpaste)

| | 22 | 23 | 24 | 25 | 26 |
|---|---|---|---|---|---|
| Sodium Gluconate | 1.064 | 1.064 | 1.064 | 1.064 | 0.600 |
| Stannous fluoride | 0.454 | 0.454 | 0.454 | 0.454 | 0.454 |
| Sodium fluoride | | | | | |
| Sodium monofluoro-phosphate | | | | | |
| Zinc Lactate | 0.670 | 0.670 | 0.670 | 0.670 | 2.500 |
| Glycerin | — | — | — | — | 36.000 |
| Polyethylene glycol 300 | | | | | 7.000 |
| Propylene Glycol | | | | | 7.000 |
| Sorbitol(LRS) USP | 39.612 | 39.612 | 39.612 | 39.612 | — |
| Sodium lauryl sulfate solution (28%) | 5.000 | 5.000 | 5.000 | 5.000 | 3.500 |
| Biodegradable abrasive cleaning particles obtained from PBS foam | 10.000 | 10.000 | 1.000 | 5.000 | 5.000 |
| Zeodent 119 | — | — | — | — | — |
| Zeodent 109 | | | 10.000 | 10.000 | 10.000 |
| Hydrogen peroxide (35% soln) | | | | | |
| Sodium hexameta-phosphate | — | — | — | — | 13.000 |
| Gantrez | — | 2.000 | 2.000 | 2.000 | — |
| Natural CaCO3-600M | — | — | — | — | — |
| Sodium phosphate (mono basic) | — | — | — | — | — |
| Sodium phosphate (Tri basic) | — | — | — | — | 1.000 |
| Zeodent 165 | — | — | — | — | — |
| Cocoamidopropyl Betaine (30% Soln) | — | — | — | — | — |
| Cetyl Alcohol | 3.000 | — | — | — | — |
| Stearyl Alcohol | 3.000 | — | — | — | — |
| Hydroxyethyl cellulose (HEC Natrasol 250M) | — | 0.500 | 0.500 | 0.500 | — |
| CMC 7M8SF | — | 1.300 | 1.300 | 1.300 | — |
| Xanthan Gum | — | — | — | — | 0.250 |
| Poloxamer 407 | — | — | — | — | — |
| Carrageenan mixture | — | 0.700 | 0.700 | 0.700 | 0.600 |
| Titanium dioxide | — | — | — | — | — |

|  | 22 | 23 | 24 | 25 | 26 |
|---|---|---|---|---|---|
| Saccharin Sodium | 0.500 | 0.500 | 0.500 | 0.500 | 0.500 |
| Flavor | 1.000 | 1.000 | 1.000 | 1.000 | 1.000 |
| Water | QS | QS | QS | QS | QS |

Zeodent 119, 109 and 165 are precipitated silica materials sold by the J. M. Huber Corporation.

Gantrez is a copolymer of maleic anhydride or acid and methyl vinyl ether.

CMC 7M8SF is a sodium carboxymethylcellulose.

Poloxamer is a difunctional block-polymer terminating in primary hydroxyl groups.

|  | 27 | 28 | 29 | 30 | 31 |
|---|---|---|---|---|---|
| Sodium Gluconate | — | — | — | — | — |
| Stannous fluoride | — | — | — | — | — |
| Sodium fluoride | — | 0.243 | 0.243 | 0.243 | — |
| Sodium monofluoro-phosphate | 1.10 | — | — | — | — |
| Zinc Lactate | — | — | — | — | — |
| Glycerin | — | — | — | — | 40.000 |
| Polyethylene glycol 300 | — | — | — | — | — |
| Propylene Glycol | | | | | |
| Sorbitol(LRS) USP | 24.000 | 42.500 | 42.500 | 42.500 | 30.000 |
| Sodium lauryl sulfate solution (28%) | 4.000 | 4.000 | — | 4.000 | — |
| Biodegradable abrasive cleaning particles obtained from PBS foam | 5.000 | 10.000 | 10.000 | 5.000 | 15.000 |
| Zeodent 119 | — | — | — | 10.000 | — |
| Zeodent 109 | | | | | |
| Hydrogen peroxide (35% soln) | — | — | — | — | — |
| Sodium hexameta-phosphate Gantrez | — | — | — | — | — |
| Natural CaCO3-600M | 35.00 | — | — | — | — |
| Sodium phosphate (mono basic) | 0.10 | 0.420 | 0.420 | 0.420 | 0.420 |
| Sodium phosphate (Tri basic) | 0.40 | 1.100 | 1.100 | 1.100 | 1.100 |
| Zeodent 165 | 2.00 | — | — | — | 2.000 |
| Cocoamidopropyl Betaine (30% Soln) | — | — | 5.000 | — | — |
| Cetyl Alcohol | 0.000 | — | — | — | — |
| Stearyl Alcohol | 0.000 | — | — | — | — |
| Hydroxyethyl cellulose (HEC Natrasol 250M) | — | 0.500 | 0.500 | 0.500 | — |
| CMC 7M8SF | 1.300 | 1.300 | 1.300 | 1.300 | 1.300 |
| Xanthan Gum | — | — | — | — | — |
| Poloxamer 407 | — | — | — | — | — |
| Carrageenan mixture | — | 0.700 | 0.700 | 0.700 | — |
| Titanium dioxide | — | — | — | — | — |
| Saccharin Sodium | 0.250 | 0.500 | 0.500 | 0.500 | 0.500 |
| Flavor | 1.000 | 1.000 | 1.000 | 1.000 | 1.000 |
| Water | QS | QS | QS | QS | QS |

|  | 32 | 33 | 34 |
|---|---|---|---|
| Sodium Gluconate | — | — | 1.500 |
| Stannous fluoride | — | — | 0.454 |
| Sodium fluoride | — | — | — |
| Sodium monofluoro-phosphate | — | — | — |
| Zinc Lactate | — | — | — |
| Glycerin | 40.000 | 10.000 | 25.000 |
| Polyethylene glycol 300 | 3.000 | — | — |
| Propylene Glycol | — | — | — |
| Sorbitol(LRS) USP | — | 39.612 | — |
| Sodium lauryl sulfate solution (28%) | 5.000 | 4.000 | 4.000 |
| Biodegradable abrasive cleaning particles obtained from PBS foam | 15.000 | 5.000 | 5.000 |
| Zeodent 119 | — | — | — |
| Zeodent 109 | — | — | — |
| Hydrogen peroxide (35% soln) | — | 8.570 | 8.570 |
| Sodium hexameta-phosphate Gantrez | 14.000 | — | — |
| Natural CaCO3-600M | — | — | — |
| Sodium phosphate (mono basic) | 0.420 | — | — |
| Sodium phosphate (Tri basic) | 1.100 | — | — |
| Zeodent 165 | 2.000 | — | — |
| Cocoamidopropyl Betaine (30% Soln) | — | — | — |
| Cetyl Alcohol | — | 3.000 | — |
| Stearyl Alcohol | — | 3.000 | — |
| Hydroxyethyl cellulose (HEC Natrasol 250M) | — | — | — |
| CMC 7M8SF | 1.000 | — | — |
| Xanthan Gum | 0.300 | — | — |
| Poloxamer 407 | 0.500 | — | 18.000 |
| Carrageenan mixture | — | — | — |
| Titanium dioxide | 0.500 | — | — |
| Saccharin Sodium | 0.500 | 0.500 | 0.500 |
| Flavor | 1.000 | 1.000 | 1.000 |
| Water | QS | QS | QS |

Hair Shampoo

|  | 35 | 36 | 37 |
|---|---|---|---|
| Water | q.s. | q.s. | q.s. |
| Polyquaterium 76[1] | 0.25 | — | — |
| Guar, Hydroxylpropyl Trimonium Chloride[2] | — | 0.25 | — |
| Polyquaterium 6[3] | — | — | 0.25 |
| Sodium Laureth Sulfate | 12 | 10.5 | 10.5 |
| Sodium Lauryl Sulfate | — | 1.5 | 1.5 |
| Silicone[4] | 0.75 | 1.00 | 0.5 |
| Cocoamidopropyl Betaine | 3.33 | 3.33 | 3.33 |
| Cocoamide MEA | 1.0 | 1.0 | 1.0 |
| Ethylene Glycol Distearate | 1.50 | 1.50 | 1.50 |
| Biodegradable abrasive cleaning particles obtained from PBS foam | 1 | — | 2 |
| Crosslinked PS-DVB (50% DVB 55, mean diameter D(v, 0.9) 75 μm) abrasive cleaning particles | — | 1 | — |
| Fragrance | 0.70 | 0.70 | 0.70 |
| Preservatives, pH & Visc. adjusters | Up to 1% | Up to 1% | Up to 1% |

[1] Copolymer of Acrylamide(AM) and TRIQUAT, MW = 1,000,000; CD = 1.6 meq./gram; Rhodia
[2] Jaguar C500, MW - 500,000, CD = 0.7, Rhodia
[3] Mirapol 100S, 31.5% active, Rhodia
[4] Dimethicone Fluid, Viscasil 330M; 30 micron particle size; Momentive Silicones The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid cleaning and/or cleansing composition comprising biodegradable abrasive cleaning particles comprising a biodegradable aliphatic polyester comprising aliphatic dicarboxylic acid monomer or mixtures thereof and alkanediol monomer or mixtures thereof, wherein said biodegradable abrasive cleaning particles have a mean circularity from about 0.1 to about 0.6, wherein the circularity is measured according to ISO 9276—and mean solidity from about 0.4 to about 0.9, wherein mean solidity is measured according to ISO 9276-6, wherein said biodegradable abrasive cleaning particles have a biodegradable rate above about 50% according to ASTM6400 test method, and wherein said biodegradable abrasive cleaning particles comprise biodegradable polyester material selected from the group consisting of polybutylene succinate (PBS), polybutylene adipate (PBA), polybutylene succinate-co-polybutylene adipate (PBSA), polyethylene succinate, polyethylene succinate-co-polyethylene adipate, polypropylene succinate, polypropylene succinate-co-polypropylene adipate and mixtures thereof.

2. A liquid cleaning and/or cleansing composition according to claim 1, wherein said biodegradable aliphatic polyester comprises dicarboxylic acid monomer containing a number of carbons atoms ranging from 2 to 6 and alkanediol monomer containing a number of carbon atoms ranging from 2 to 4.

3. A liquid cleaning and/or cleansing composition according to claim 1, wherein said biodegradable abrasive cleaning particles comprise biodegradable polyester material selected from the group consisting of polybutylene succinate (PBS), polybutylene adipate (PBA), polybutylene succinate-co-polybutylene adipate (PBSA), polyethylene succinate, polyethylene succinate-co-polyethylene adipate, polypropylene succinate, polypropylene succinate-co-polypropylene adipate and mixtures thereof.

4. A liquid cleaning and/or cleansing composition according to claim 1, wherein said biodegradable abrasive cleaning particles comprise biodegradable polyester material selected from the group consisting of PBS, PBA, PBSA and mixtures thereof.

5. A liquid cleaning and/or cleansing composition according to claim 1, wherein said biodegradable abrasive cleaning particles comprise biodegradable polyester material selected from the group consisting of PBS, PBSA and mixtures thereof.

6. A liquid cleaning and/or cleansing composition according to claim 1, wherein said biodegradable abrasive cleaning particles have a mean circularity from about 0.2 to about 0.35 and wherein the circularity is measured according to ISO 9276-6.

7. A liquid cleaning and/or cleansing composition according to claim 1, wherein said biodegradable abrasive cleaning particles have mean solidity preferably from about 0.55 to about 0.65, wherein mean solidity is measured according to ISO 9276-6.

8. A liquid cleaning and/or cleansing composition according to claim 1, wherein said biodegradable abrasive particles have HV Vickers hardness from about 3 to about 50 kg/mm$^2$, wherein the Vickers hardness is measured according to method disclosed herein.

9. A liquid cleaning and/or cleansing composition according to claim 1, wherein said biodegradable abrasive particles have HV Vickers hardness from about 5 to about 15 kg/mm$^2$, wherein the Vickers hardness is measured according to method disclosed herein.

10. A liquid cleaning and/or cleansing composition according to claim 1, wherein said biodegradable abrasive particles have a mean particle size as expressed by the area-equivalent diameter from about 10 to about 1000 μm according to ISO 9276-6.

11. A liquid cleaning and/or cleansing composition according to claim 1, wherein said biodegradable abrasive particles have a mean particle size as expressed by the area-equivalent diameter from about 150 to about 250 μm according to ISO 9276-6.

12. A liquid cleaning and/or cleansing composition according to claim 1, wherein said biodegradable abrasive cleaning particles are reduced into particles from foamed biodegradable aliphatic polyester.

13. A liquid cleaning and/or cleansing composition according to claim 1, wherein said composition comprises from about 0.1%, to about 20% by weight of the composition of said biodegradable abrasive particles.

14. A liquid cleaning and/or cleansing composition according to claim 1, wherein said composition comprises from about 1% to about 3% by weight of the composition of said biodegradable abrasive particles.

15. A liquid cleaning and/or cleansing composition according to claim 1 further comprises a suspending aid, wherein said suspending aid is selected from the group consisting of polycarboxylate polymer thickeners; hydroxyl-containing fatty acid, fatty ester or fatty soap materials; carboxymethylcellulose, ethyl cellulose, hydroxyethyl cellulose, hydroxypropyl cellulose, hydroxymethyl cellulose, succinoglycan, Xanthan gum, gellan gum, guar gum, locust bean gum, tragacanth gum, succinoglucan gum, and derivatives thereof, or mixtures thereof.

16. A liquid cleaning and/or cleansing composition according to claim 1, wherein the cleaning composition is loaded on a cleaning substrate, wherein the substrate is a paper or non-vowen towel or wipe or a sponge.

17. A process of cleaning and/or cleansing a surface with a liquid, cleaning and/or cleansing composition according to claim 1, wherein said surface is contacted with said composition, wherein said composition is applied onto said surface.

18. A process according to claim 17, wherein said surface is an inanimate surface, selected from the group consisting of household hard surfaces; dish surfaces; leather; synthetic leather; and automotive vehicles surfaces.

19. A process according to claim 17, wherein said surface is an animate surface, selected from the group consisting of human and animal hair, hard and soft tissue surface of the oral cavity.

* * * * *